(12) United States Patent
Kadam et al.

(10) Patent No.: US 11,970,444 B2
(45) Date of Patent: Apr. 30, 2024

(54) PROCESS FOR PREPARATION OF GLYCOPYRROLATE TOSYLATE

(71) Applicant: HARMAN FINOCHEM LIMITED, Mumbai (IN)

(72) Inventors: Vijay Trimbak Kadam, Aurangabad (IN); Dhananjay Uddhavrao Ed Aki, Aurangabad (IN); Ravindra Bhausaheb Pagire, Ahmednagar (IN); Mayur Sanjay Kulkarni, Solapur (IN); Harpreet Singh Minhas, Mumbai (IN); Gurpreet Singh Minhas, Mumbai (IN)

(73) Assignee: HARMAN FINOCHEM LIMITED, Mumbai (IN)

( * ) Notice: Subject to any disclaimer, the term of this patent is extended or adjusted under 35 U.S.C. 154(b) by 597 days.

(21) Appl. No.: 17/291,736

(22) PCT Filed: Nov. 6, 2019

(86) PCT No.: PCT/IN2019/050822
§ 371 (c)(1),
(2) Date: May 6, 2021

(87) PCT Pub. No.: WO2020/095322
PCT Pub. Date: May 14, 2020

(65) Prior Publication Data
US 2022/0009888 A1 Jan. 13, 2022

(30) Foreign Application Priority Data
Nov. 6, 2018 (IN) .............................. 201821041917

(51) Int. Cl.
*C07D 207/12* (2006.01)
*C07C 303/32* (2006.01)
*C07C 303/44* (2006.01)

(52) U.S. Cl.
CPC .......... *C07D 207/12* (2013.01); *C07C 303/32* (2013.01); *C07C 303/44* (2013.01)

(58) Field of Classification Search
CPC .... C07D 207/12; C07C 303/32; C07C 303/44
USPC ....................................................... 548/556
See application file for complete search history.

(56) References Cited

U.S. PATENT DOCUMENTS

| | | | |
|---|---|---|---|
| 5,525,347 A | 6/1996 | Kellner et al. |
| 5,919,760 A | 7/1999 | Simon |
| 5,976,499 A | 11/1999 | Rubenstein et al. |
| 6,063,808 A | 5/2000 | Fabiano et al. |
| 6,204,285 B1 | 3/2001 | Fabiano et al. |
| 6,214,792 B1 | 4/2001 | Simon |
| 8,558,008 B2 | 10/2013 | Statler et al. |
| 9,006,461 B2 | 4/2015 | Statler et al. |
| 2010/0276329 A1 | 11/2010 | Johnston et al. |
| 2016/0052879 A1 | 2/2016 | Shaw et al. |

FOREIGN PATENT DOCUMENTS

WO 2018/167776 A1 9/2018

OTHER PUBLICATIONS

PCT/IN2019/050822 International Search Report dated Jan. 15, 2020; 3 pgs.
Written Opinion of International Search Authority re PCT/IN2019/050822 dated Jan. 2015, 21; 4 pgs.

*Primary Examiner* — Kristin A Vajda
(74) *Attorney, Agent, or Firm* — Kramer & Amado, P.C.

(57) ABSTRACT

Disclosed herein is an efficacious process for preparation of highly purified Glycopyrrolate tosylate in high yield. The process is being cost effective, environment friendly and easily scalable to high volume industrial production.

11 Claims, No Drawings

PROCESS FOR PREPARATION OF GLYCOPYRROLATE TOSYLATE

FIELD OF THE INVENTION

The present application provides an efficacious industrial process for the preparation of Glycopyrrolate Tosylate or Glycopyrronium Tosylate. In particular, the present invention provides an eco-friendly industrial process for preparation of Glycopyrronium Tosylate with high yields and purity.

BACKGROUND OF THE INVENTION

Glycopyrrolate is a quaternary ammonium cation of the muscarinic anticholinergic group. Glycopyrrolate, typically as a bromide salt, has been used in the treatment of a variety of conditions including diarrhoea (U.S. Pat. Nos. 6,214,792 and 5,919,760), urinary incontinence (U.S. Pat. Nos. 6,204,285 and 6,063,808), and anxiety (U.S. Pat. No. 5,525,347). Additionally, U.S. Pat. No. 5,976,499 discloses a method for diagnosing cystic fibrosis in a patient by stimulating sweat production through the injection of a Glycopyrrolate solution into a patient. Glycopyrrolate has also been used for the treatment of hyperhidrosis as reported in US 20100276329.

Glycopyrrolate has previously been made available as a bromide salt or an acetate salt. The bromide salt of Glycopyrrolate is sold as Rubinol®. The term "Glycopyrrolate" as used in the label for Rubinol® refers to the bromide salt which is more formally referred to as glycopyrronium bromide.

Glycopyrronium Tosylate, also known as (1,1-dimethylpyrrolidin-1-ium-3-yl) 2-cyclopentyl-2-hydroxy-2-phenylacetate; 4-methylbenzenesulfonate is an anti-muscarinic agent. Other Glycopyrrolate salts are used as anti-asthmatic or antispasmodic agents administered either intravenously, orally or topically in accordance with the medical indication. Glycopyrronium bromide and Glycopyrronium tosylate have been clinically tested for the topical treatment of hyperhidrosis.

Glycopyrronium tosylate has the following chemical structure:

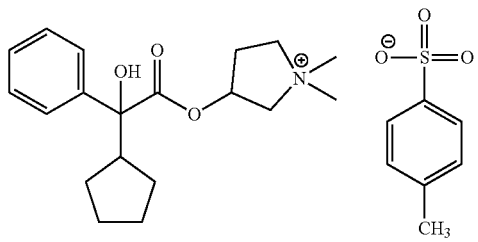 [SMILES: C[N+]1(C)CCC(OC(=O)C(O)(c2ccccc2)C2CCCC2)C1 ; Cc1ccc(S(=O)(=O)[O-])cc1]

Several synthetic procedures have been reported in the prior arts, one of which is the conversion of the Glycopyrrolate bromide (commercially available as "Glycopyrrolate") into Glycopyrrolate tosylate. U.S. Pat. No. 8,558,008 disclosed the process for the preparation of Glycopyrrolate Tosylate by reacting Glycopyrrolate bromide with a metal salt preferably silver salt and material thus obtained is lyophilized to get Glycopyrrolate as glassy solid which is further isolated by toluene.

U.S. Pat. No. 9,926,270 reported a method of producing glycopyrronium tosylate comprising contacting Glycopyrrolate base with methyl tosylate to produce glycopyrronium tosylate. These syntheses have been prone to give rise to high levels of by-products, which is highly undesirable and requires further purification processes and lyophilization which is cumbersome at large scale production.

WO2018167776 disclosed the process for the preparation of Glycopyrrolate tosylate comprising reaction of Glycopyrronium halide and tosylic acid or salt thereof in a biphasic system and in the presence of at least one phase transfer catalyst. Despite using biphasic system and PTC, the yields are not very high and the use of this system escalates the process economics.

Acknowledgement of the above references herein is not to be inferred as meaning that these are in any way relevant to the patentability of the presently disclosed subject matter.

So there is an unmet need to provide an efficacious process for preparation of highly purified Glycopyrrolate tosylate in high yield and said process being cost effective, environment friendly and easily scalable to high volume industrial production.

Surprisingly the inventors of the present invention have invented a very efficient and green process for the preparation of Glycopyrrolate Tosylate which can be performed with simple operation steps and without the use of any hazardous organic solvents. Additionally, the present invention avoids the use of phase transfer catalyst(s) making the process also economically viable.

SUMMARY OF THE INVENTION

Accordingly, the present invention provides a process for the preparation of Glycopyrrolate tosylate comprising:
(a) preparing a sodium salt of tosylic acid by reacting tosylic acid with sodium methoxide in a non-polar organic solvent to obtain sodium tosylate, which is optionally purified by using an alcoholic solvent;
(b) reacting the sodium tosylate obtained in step (a) with glycopyrronium bromide, in the presence of water, to obtain crude Glycopyrronium tosylate; and
(c) purifying the crude Glycopyrronium tosylate from water to obtain highly pure Glycopyrronium tosylate.

DETAILED DESCRIPTION OF THE PRESENT INVENTION

The invention will now be described in detail in connection with certain preferred and optional embodiments, so that various aspects thereof may be more fully understood and appreciated.

Unless specified otherwise, all technical and scientific terms used herein have the same meaning as commonly understood by one of ordinary skill in the art, to which this invention belongs. To describe the invention, certain terms are defined herein specifically as follows.

Unless stated to the contrary, any of the words, "including", "includes", "comprising", and "comprises" mean "including without limitation" and shall not be construed to limit any general statement that it follows to the specific or similar items.

Accordingly, the invention provides a process for the preparation of Glycopyrrolate tosylate comprising:
(a) preparing a sodium salt of tosylic acid by reacting tosylic acid with sodium methoxide in a non-polar organic solvent to obtain sodium tosylate which is optionally purified by using an alcoholic solvent;
(b) reacting the sodium tosylate obtained in step (a) with glycopyrronium bromide in the presence of water to obtain crude Glycopyrronium tosylate; and (c) purifying the crude Glycopyrronium tosylate from water to obtain highly pure Glycopyrronium tosylate.

In accordance with the present invention, sodium tosylate is prepared by reacting p-toluene sulfonic acid monohydrate with sodium methoxide in non-polar solvent under reflux temperature. p-toluene sulfonic acid monohydrate is taken in non-polar solvent and heated to reflux whereby water separated during reflux, is removed. The reaction mass is cooled to 50 to 65° C. and then sodium methoxide is added. The methanol formed during the reaction is removed from the reaction mass by distillation. The reaction mass is cooled to 20-35° C. and filtered to obtain the solid. The wet solid is washed with heptane and dried to obtain crude sodium tosylate. The crude sodium tosylate thus obtained is further purified from an alcoholic solvent to obtain pure sodium salt of tosylic acid.

The non-polar organic solvent used in the process of preparation of sodium tosylate is selected from the group consisting of hydrocarbon solvents such as pentane, hexane, heptane, cyclopentane, cyclohexane, toluene and the like.

The reaction of tosylic acid with sodium methoxide is carried out at a temperature of about 50° C. to reflux temperature of the solvent used.

The sodium tosylate thus obtained is recovered at ambient temperature.

The alcoholic solvent used in the purification of sodium tosylate is selected from group consisting of $C_1$-$C_4$ alcohols.

In another embodiment, glycopyrronium tosylate is prepared by reacting glycopyrronium bromide and sodium tosylate. Glycopyrronium bromide and sodium tosylate are taken in water and heated to 30-50° C. The reaction mass is charged with activated carbon, stirred for 20-25 minutes and carbon is removed by filtration. The filtrate is collected and cooled to room temperature to obtain Glycopyrronium tosylate, which is filtered, washed with water and dried to obtain Glycopyrronium tosylate.

In yet another embodiment, the invention provides a process for purification of Glycopyrronium tosylate by dissolving the same in purified water and heated the mass to 30-50° C., Stirred for 30 min to obtain clear solution. Then the mass is gradually cooled to 10-15° C. & maintained at the same temperature for 2-3 hr, to obtain Glycopyrronium Tosylate with HPLC purity of more than 99.8%.

In another embodiment, the process for preparation of Glycopyrronium tosylate can be prepared in one pot, wherein, the intermediate, sodium tosylate is not isolated. Glycopyrronium tosylate obtained according to the process of the present invention has HPLC purity greater than 99.8% with water content in an amount of 3 to 4% which complies with the pharmacopeial specifications.

The Glycopyrronium tosylate according to the present invention can be produced with good yields in the range of 65 to 80%.

The inventive process of present invention is uncomplicated, eco-friendly and cost effective and thus can be scaled easily for industrial production of Glycopyrronium tosylate.

Following examples are given to further illustrate the present invention and therefore should not be construed to limit the scope of the present invention.

EXAMPLES

Example—1

(a) Preparation of Sodium p-Toluene Sulfonate (Sodium Tosylate):

To a clean and neat RBF, charged heptane (800 ml), p-toluene sulfonic acid monohydrate (100 g) and heated the reaction mass to reflux. The water was separated during reflux. The reaction mass was cooled to 60-65° C. and slowly added sodium methoxide (28.38 g) and reaction mass was again heated to reflux, methanol was removed from the reaction mass by distillation. The reaction mass was cooled to 30-35° C. and filtered to obtain the solid. The wet solid was washed with heptane (100 ml) and dried to obtain crude sodium tosylate (90.5 gm, yield 68.2%). The solid obtained was further purified by methanol to obtain pure sodium salt of tosylic acid (75 gm).

(b) Preparation of Crude Glycopyrronium Tosylate:

To a clean and neat RBF, charged water (300 ml), glycopyrronium bromide (30 gm) and sodium tosylate (15.34 gm) and heated to 40-45° C., charged activated carbon, stirred for 20-25 minutes and carbon was removed by filtration. Collected the filtrate and cooled to room temperature. White precipitates so obtained were filtered, washed with water and dried to get Glycopyrronium tosylate (26 gm, yield 78.9%) having HPLC purity greater than 99.68%; water content of 3.47%

(c) Purification of Crude Glycopyrronium Tosylate:

To a clean & neat RBF, charged Purified water (270 ml), crude Glycopyrronium tosylate (45 gm) & heated to 40-45° C., Stirred for 30 min at 40-45° C. to obtain clear solution. Then gradually cooled to 10-15° C. & maintained for 2-3 hrs. filtered the solid & washed with purified water, dried to obtain pure Glycopyrronium Tosylate (39 gm), (yield 86.66%) having HPLC purity greater than 99.92% with water content of 3.53%.

Example—2

(a) Preparation of Sodium p-Toluene Sulfonate (Sodium Tosylate):

To a clean and neat RBF, charged heptane (4000 ml), p-toluene sulfonic acid monohydrate (500 g) and heated the reaction mass to reflux. The water was separated during reflux. The reaction mass was cooled to 60-65° C. and slowly added sodium methoxide (141.9 g) and reaction mass was again heated to reflux, methanol was removed from the reaction mass by distillation. The reaction mass was cooled to 30-35° C. and filtered to obtain the solid. The wet solid was washed with heptane (500 ml) and dried to obtain crude sodium tosylate (492 gm). The solid obtained was further purified by methanol to obtain pure sodium salt of tosylic acid (361 gm).

(b) Preparation of Crude Glycopyrronium Tosylate:

To a clean and neat RBF, charged water (4500 ml), glycopyrronium bromide (450 gm) and sodium tosylate (230.12 gm) and heated to 40-45° C., charged activated carbon, stirred for 20-25 minutes and carbon was removed by filtration. Collected the filtrate and cooled to room temperature. White precipitates so obtained were filtered, washed with water and dried to obtain Glycopyrronium tosylate (451 gm, yield 78.9%) having HPLC purity 99.86%; water content of 3.41%.

(c) Purification of Crude Glycopyrronium Tosylate:

To a clean & neat RBF, charged purified water (2670 ml), crude Glycopyrronium tosylate (445 gm) & heated to 40-45° C., Stirred for 30 min at 40-45° C. to obtain clear solution. Then cooled the solution to 25-30° C.; gradually further cooled to 10-15° C. & maintained for 2-3 hr. Filtered the solid & washed with purified water, dried to obtain pure Glycopyrronium Tosylate (390 gm), (yield 87.64%) having HPLC purity greater than 99.90%; water content of 3.46%.

Example—3

Preparation of Glycopyrronium Tosylate (In-Situ Process):

To a clean and neat RBF, charged heptane (400 ml), p-toluene sulfonic acid monohydrate (50 g) and heated the reaction mass to reflux. The water was separated during reflux. The reaction mass was cooled to 60-65° C. and slowly added sodium methoxide (141.9 g) and the reaction mass was again heated to reflux, methanol was removed from the reaction mass by distillation. The reaction mass was concentrated under vacuum and degassed to remove heptane completely. Charged water (1000 ml) and glycopyrronium bromide (100 gm), stirred for 60-90 min at room temperature. Raised temperature to 40-45° C. and charged activated carbon, stirred for 20-25 minutes and carbon was removed by filtration. Collected the filtrate, cooled to room temperature and stirred for 60 min. White precipitate was observed, cooled to 10-15° C. and maintained for 60-90 min. Solid was isolated by filtration washed with water and dried to obtain Glycopyrronium tosylate (83 gm, yield 65.35%) having HPLC purity 99.80%; water content of 3.53%.

Example—4

Preparation of Glycopyrronium Tosylate (In-Situ Process):

To a clean and neat RBF, charged heptane (400 ml), p-toluene sulfonic acid monohydrate (50 g) and heated the reaction mass to reflux. The reaction mass was cooled to 60-65° C. and slowly added sodium methoxide (15.61 g), reaction mass was again heated to reflux. The reaction mass was concentrated under vacuum and degassed. Charged water (1000 ml) and Glycopyrronium bromide (104.6 gm), in same RBF and stirred for 60-90 min at room temperature. Raised temperature to 40-45° C. and charged activated carbon, stirred for 20-25 minutes and carbon was removed by filtration. Collected the filtrate, cooled to room temperature and stirred for 90 min. White precipitates so obtained, were cooled to 10-15° C. and maintained for 60-90 min. Solid was isolated by filtration, washed with water and dried to obtain Glycopyrronium Tosylate (94 gm, yield 70%) having HPLC purity of more than 99.91%, water content of 3.53%.

Example—5

Preparation of Glycopyrronium Tosylate (In-Situ Process):

To a clean and neat RBF, charged heptane (400 ml), p-toluene sulfonic acid monohydrate (50 g) and heated the reaction mass to reflux. The reaction mass was cooled to 60-65° C. and slowly added sodium methoxide (14.19 g), and again heated to reflux. The reaction mass was concentrated under vacuum. Charged water (1000 ml) and Glycopyrronium bromide (115 gm), in the same RBF and stirred for 60-90 min at room temperature. Raised temperature to 40-45° C. and charged activated carbon, stirred for 20-25 minutes and filtered. Collected the filtrate, cooled to room temperature and stirred for 90 min. White precipitates so obtained, cooled to 10-15° C. and maintained for 60-90 min. Solid was isolated by filtration washed with water and dried to obtain Glycopyrronium Tosylate (114.0 gm, yield 78%) having HPLC purity more than 99.90% and water content of 3.53%.

Example—6

Preparation of Glycopyrronium Tosylate (In-Situ Process):

To a clean and neat RBF, charged Cyclohexane (200 ml), p-toluene sulfonic acid monohydrate (25 g) and heated the reaction mass to reflux. The reaction mass was cooled to 60-65° C. and slowly added sodium methoxide (7.1 g), heated to reflux. The reaction mass was concentrated under vacuum and degassed to remove Cyclohexane completely. Charged water (1000 ml) and Glycopyrronium bromide (52.3 gm) in the same RBF, stirred for 60-90 min at room temperature. Raised temperature to 40-45° C. and charged activated carbon, stirred for 20-25 minutes and filtered. Collected the filtrate, cooled to room temperature and stirred for 90 min. White precipitate was observed, cooled to 10-15° C. and maintained for 60-90 min. Solid was isolated by filtration washed with water and dried to obtain Glycopyrronium Tosylate (54.0 gm, yield 81%) having HPLC purity more than 99.88%; water content of 3.53%.

Example—7

Preparation of Glycopyrronium Tosylate (In-Situ Process):

To a clean and neat RBF, charged Toluene (400 ml), p-toluene sulfonic acid monohydrate (50 g) and heated the reaction mass to reflux. The reaction mass was cooled to 60-65° C. and slowly added sodium methoxide (14.19 g), and heated to reflux. The reaction mass was concentrated under vacuum. Charged water (1000 ml) and Glycopyrronium bromide (104.6 gm), in the same RBF and stirred for 60-90 min at room temperature. Raised temperature to 40-45° C. and charged activated carbon, stirred for 20-25 minutes and filtered. Collected the filtrate, cooled to room temperature and stirred for 90 min. White precipitate so obtained was cooled to 10-15° C. and maintained for 60-90 min. Solid was isolated by filtration washed with water and dried to obtain Glycopyrronium Tosylate (105.0 gm, yield 79%) having HPLC purity more than 99.90%; water content of 3.53%.

We claim:

1. A process for preparing glycopyrronium tosylate, comprising:
    a) preparing a sodium salt of p-toluenesulfonic acid by reacting p-toluenesulfonic acid with sodium methoxide in a nonpolar organic solvent; and
    b) reacting the sodium salt of p-toluenesulfonic acid with glycopyrronium bromide in the presence of water to obtain glycopyrronium tosylate.

2. The process as claimed in claim 1, further comprising a step of purifying the glycopyrronium tosylate with water.

3. The process as claimed in claim 1, further comprising a step of purifying the sodium salt of p-toluenesulfonic acid by using an alcoholic solvent, prior to reacting the sodium salt of p-toluenesulfonic acid with glycopyrronium bromide.

4. The process as claimed in claim 1, further comprising a step of purifying the sodium salt of p-toluenesulfonic acid by using an alcoholic solvent, prior to reacting the sodium salt of p-toluenesulfonic acid with glycopyrronium bromide;

wherein the alcoholic solvent is selected from the group consisting of C1-C4 alcohols.

5. An in situ process for preparing glycopyrronium tosylate, comprising:
a) preparing a sodium salt of p-toluenesulfonic acid by reacting p-toluenesulfonic acid with sodium methoxide in a nonpolar organic solvent; and
b) reacting the sodium salt of p-toluenesulfonic acid with glycopyrronium bromide in the presence of water to obtain glycopyrronium tosylate, wherein:
the step of reacting the sodium salt of p-toluenesulfonic acid with glycopyrronium bromide is carried out in situ in the presence of water.

6. The process as claimed in claim 1, wherein the nonpolar organic solvent is selected from the group consisting of pentane, hexane, heptane, cyclopentane, cyclohexane, toluene, and mixtures thereof.

7. The process as claimed in claim 1, wherein the step of preparing a sodium salt of p-toluenesulfonic acid is carried out at a temperature ranging from about 50° C. to a reflux temperature of the nonpolar organic solvent.

8. The process as claimed in claim 1, wherein the step of reacting the sodium salt of p-toluenesulfonic acid with glycopyrronium bromide is conducted at a temperature ranging from 30° C. to 50° C.

9. The process as claimed in claim 2, wherein the step of purifying the crude glycopyrronium tosylate is conducted at a temperature ranging from 30° C. to 50° C.

10. The process as claimed in claim 2, wherein the nonpolar organic solvent is selected from the group consisting of pentane, hexane, heptane, cyclopentane, cyclohexane, toluene, and mixtures thereof.

11. The process as claimed in claim 2, wherein the step of preparing a sodium salt of p-toluenesulfonic acid is carried out at a temperature ranging from about 50° C. to a reflux temperature of the nonpolar organic solvent.

* * * * *